United States Patent

Hohorst

Patent Number: 5,473,643
Date of Patent: Dec. 5, 1995

[54] CORROSION TESTING USING ISOTOPES

[75] Inventor: Frederick A. Hohorst, Idaho Falls, Id.

[73] Assignee: Westinghouse Idaho Nuclear Company, Idaho Falls, Id.

[21] Appl. No.: 292,758

[22] Filed: Aug. 19, 1994

[51] Int. Cl.$^6$ ........................................ G21G 1/06
[52] U.S. Cl. ................. 376/159; 376/167; 376/249; 250/303
[58] Field of Search ..................... 376/305, 159, 376/167, 249; 250/303, 260; 73/86, 863.22, 866; 422/53; 436/6

[56] References Cited

U.S. PATENT DOCUMENTS

| | | | |
|---|---|---|---|
| 2,938,125 | 5/1960 | Marak | 250/106 |
| 2,994,778 | 8/1961 | Marsh | 73/86 |
| 3,348,052 | 10/1967 | Raifsnider et al. | 250/260 |
| 3,385,358 | 5/1968 | Shell | 166/1 |
| 3,621,252 | 11/1969 | Eddy, Jr. | 250/71.5 R |
| 3,632,470 | 1/1972 | Rubin et al. | 376/251 |
| 3,663,363 | 5/1972 | Crouthamel et al. | 376/251 |
| 3,848,187 | 11/1974 | Rohrback et al. | 324/65 CR |
| 4,107,533 | 8/1978 | Tabuchi et al. | 250/364 |
| 4,267,148 | 5/1981 | Dickson et al. | 422/53 |
| 4,482,806 | 11/1984 | Wagner et al. | 250/260 |
| 4,495,143 | 1/1985 | Gross et al. | 376/251 |
| 4,537,740 | 8/1985 | Colburn | 376/256 |
| 4,563,427 | 1/1986 | Weiss et al. | 436/6 |
| 4,620,185 | 10/1986 | Plahmer | 340/682 |
| 4,922,748 | 5/1990 | Hopenfeld | 73/86 |
| 5,120,421 | 6/1992 | Glass et al. | 204/406 |
| 5,124,114 | 6/1992 | Bilsborough | 376/256 |
| 5,164,152 | 11/1992 | Kim et al. | 376/305 |
| 5,306,414 | 4/1994 | Glass et al. | 204/404 |

FOREIGN PATENT DOCUMENTS

| | | | |
|---|---|---|---|
| 0317339 | 5/1989 | European Pat. Off. | |
| 1126916 | 9/1968 | Germany | 250/260 |
| 1753374 | 2/1990 | U.S.S.R. | |

*Primary Examiner*—Donald P. Walsh
*Assistant Examiner*—Meena Chelliah

[57] ABSTRACT

A method for determining the corrosion behavior of a material with respect to a medium in contact with the material by: implanting a substantially chemically inert gas in a matrix so that corrosion experienced by the material causes the inert gas to enter the medium; placing the medium in contact with the material; and measuring the amount of inert gas which enters the medium.

A test sample of a material whose resistance to corrosion by a medium is to be tested, composed of: a body of the material, which body has a surface to be contacted by the medium; and a substantially chemically inert gas implanted into the body to a depth below the surface.

A test sample of a material whose resistance to corrosion by a medium is to be tested, composed of: a substrate of material which is easily corroded by the medium, the substrate having a surface; a substantially chemically inert gas implanted into the substrate; and a sheet of the material whose resistance to corrosion is to be tested, the sheet being disposed against the surface of the substrate and having a defined thickness.

17 Claims, 1 Drawing Sheet

CORROSION TESTING USING ISOTOPES

This invention was conceived or first reduced to practice in the course of, or under Contract No. DE-07-84ID12435 between the Westinghouse Idaho Nuclear Company and the United States Government, represented by the Department of Energy. The United States Government may have rights in this invention.

BACKGROUND OF THE INVENTION

The present invention relates to methods for measuring corrosion properties of materials and test specimens for such measurements.

In many industrial fields, corrosion and corrosion rates are an important subject of study, this being particularly true in chemical and nuclear industries. It is presently known to perform such testing by traditional coupon testing as well as newer electronic methods.

Traditional coupon testing requires recovery of a coupon of the material being tested at regular intervals in order to evaluate the corrosion activity. Frequently, testing must be performed in toxic, potentially flammable, or explosive environments, creating risks for the operating personnel.

Electronic testing methods may not be universally applicable in this field since they are used to study electrolytic corrosion. These methods involve the use of electricity, which has the potential of starting a fire or causing an explosion. Therefore, if testing is to be performed in a volatile atmosphere, which is likely to be ignited or explode, electronic testing is not advisable.

SUMMARY OF THE INVENTION

It is an object of the present invention to provide corrosion testing procedures which avoid the above-discussed drawbacks and disadvantages.

Another object of the invention is to provide corrosion testing procedures which do not require direct access by personnel to the sample location or the use of electrical or electronic equipment at the measuring location.

Another object of the invention is to permit corrosion testing of virtually any solid sample material while permitting corrosion to occur to any desired depth.

Yet another object of the invention is to provide corrosion testing techniques which can be employed for either short term or long term testing.

The above and other objects are achieved, according to the invention, by a method for determining the corrosion behavior of a material with respect to a medium in contact with the material, comprising: implanting a substantially chemically inert, or noble, gas in a matrix so that corrosion experienced by the material causes the inert gas to enter the medium; placing the medium in contact with the material; and measuring the amount of inert gas which enters the medium.

Objects according to the invention are further achieved by provision of: a test sample of a material whose resistance to corrosion by a medium is to be tested, comprising a body of the material, which body has a surface to be contacted by the medium, and a substantially chemically inert gas implanted into the body to a depth below the surface; or a test sample of a material whose resistance to corrosion by a medium is to be tested, comprising a substrate of material which is easily corroded by the medium, the substrate having a surface, a substantially chemically inert gas implanted into the substrate, and a sheet of the material whose resistance to corrosion is to be tested, the sheet being disposed against the surface of the substrate and having a defined thickness.

DESCRIPTION OF THE PREFERRED EMBODIMENTS

Figure 2:
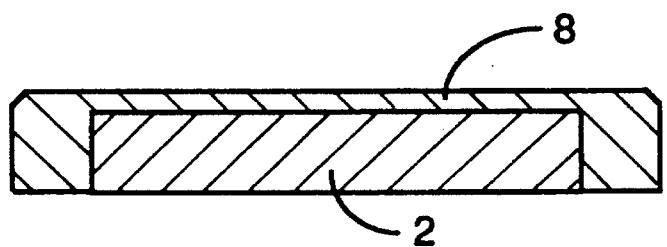
FIGS. 2 and 3 are cross-sectional views of sample arrangements for use in practicing further embodiments of the invention.
Figure 3:
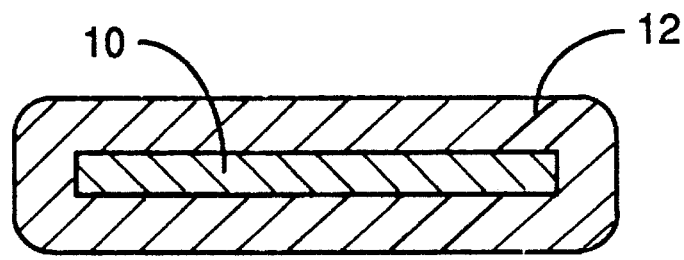

According to the invention, the rate of corrosion of a solid material is measured by placing a corrosive, or corroding, medium in contact with the material and monitoring the quantity of a preferably noble gas which enters the corrosive medium as a result of the corrosion process. Exemplary possibilities for providing a gas to act as a corrosion indicator are shown in FIGS. 1, 2 and 3.

Figure 1:
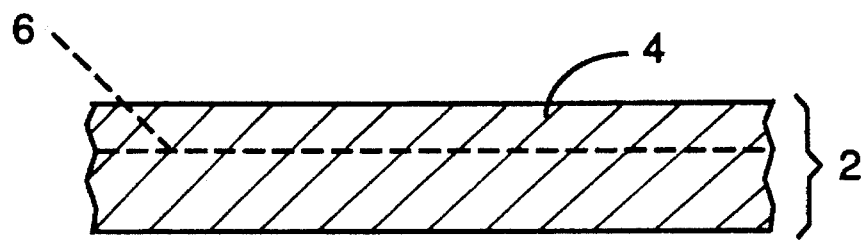
FIG. 1 is a cross-sectional detail view of a portion of a sample which is to be tested for corrosion according to one embodiment of the invention.

The embodiment shown in FIG. 1 is constituted by a body 2 of a material whose resistance to corrosion is to be measured. Body 2 can have any desired shape or form, and can be any useful article, such as a container, whose corrosion resistance is to be measured, or can be a sample of a standard material used to measure the corrosivity of a medium.

According to the invention, a gas is introduced, as by ion implantation, via one surface of body 2, into a region 4 of body 2, approximately down to a boundary, or level, 6 within body 2. Level 6 constitutes an imaginary plane in body 2 and does not represent a plane where any change occurs in the physical composition of body 2. Level 6 simply represents the approximate boundary of region 4 which contains implanted or embedded gas ions, atoms or molecules.

Region 4 extends from the surface of body 2 which will be placed in contact with a corroding medium. The medium may be either a standing or flowing liquid or gas. When region 4 of body 2 experiences corrosion, the noble gas previously embedded therein will be released into the medium. The gas may then be released into a gas space, e.g. at the closed top of a container, where the concentration of the gas can be monitored in any conventional manner.

The relation between the depth of corrosion of region 4 and the quantity of gas thus entering the corroding medium will depend on the gas distribution profile in region 4 prior to exposure to a corroding medium.

The gas may be embedded in region 4 using an isotope separator, i.e. a mass spectrometer specifically adapted for separating different isotopes from one another and embedding a selected isotope species in a substrate. The material from which body 2 is made may be an element, a crystal, a compound, or an alloy to be studied. The operating controls of an isotope separator may be set to control the depth at which the selected isotope is embedded. This depth can range from being too shallow to be measured down to several hundred angstroms (Å).

If body 2 is placed in, or is a portion of the wall of, a tank containing a corrosive liquid medium, with a certain space, known as a headspace, being left at the top of the tank, measurement of the concentration of the gas in the headspace provides a measure of the rate of corrosion of body 2 under existing conditions.

For a single setting of such an isotope separator, the depth profile of gas in region 4 has approximately a Gaussian distribution. By varying the setting during implantation, it is possible to achieve a distribution profile which will approximate a linear variation, i.e. the concentration of gas will decrease in approximately a linear manner from the surface of body 2 down to level 6.

Broadly stated, the gas which is implanted into surface region 4 may be any noble gas or an isotope thereof. The primary criteria for selection of the noble gas are that: it provide acceptable precision and accuracy during analysis of the amount of noble gas liberated from body 2; and it have an acceptably high diffusion rate in the medium which is brought into contact with body 2 and in any gaseous medium in which actual measurement of noble gas concentration is to be made. Selection of a radioisotope of a noble gas makes possible a high detection sensitivity, i.e. detection of low noble gas concentration. However, stable isotopes permitting high detecting sensitivity can also be used.

The primary advantage offered by noble gases is their inability to form chemical compounds in the absence of unusual conditions. Krypton-85 is the most common and longest lived radioisotope. Its presence can be measured routinely and reliably in the laboratory with a precision and accuracy on the order of a few percent with a method detection limit estimated at 0.2 picocurie per standard cc (pCi/scc) by liquid scintillation counting. The linear range of quantization for this method is estimated at 2 pCi/scc to $10^6$ pCi/scc. The method detection limit is equivalent to placing $2\times10^{-4}$ Ci of $^{85}$Kr in a 1000 m$^3$ tank. Typical tanks containing radioactive waste usually contain radioactivity many orders of magnitude greater than this. Waste resulting from reprocessing usually contains only background levels of $^{85}$Kr which may result from spontaneous fission. Since $^{85}$Kr forms no compounds in such tanks, it immediately diffuses in order to equalize its partial pressure throughout that environment.

Thus, noble gases can be beneficially used for monitoring corrosion rates in hazardous environments without subjecting personnel to toxic gases or explosion hazards.

The measurement of noble gas concentration may be performed incrementally, i.e. periodically, or continuously. Incremental measurement is more suitable for long term studies while continuous measurement is more useful for short term studies. A measurement system having a wide and linear response range is desirable, but not essential. A number of different types of detection can be employed. Two examples of systems for effecting such detection are liquid scintillation counters and silicon surface barrier detectors.

In connection with detection of the noble element gas released from the test material, it is desirable to condition the gas samples to remove interfering components. Potential interfering components may include radioactive particulate materials or volatile radioisotopes such as tritium, carbon-14 and iodine-129, or their precursors.

The choice of the noble gas to be employed in the method according to the invention will be based on several criteria. One important criterion is the existing background concentration of that gas in the test environment. For example, if the material whose corrosion is to be measured forms a wall or other component of a tank, or is placed in a tank for testing purposes, the criteria for selecting the particular noble gas to be implanted would depend on the normal background concentration of that gas in the tank. For many purposes, $^{85}$Kr is the preferred gas.

Testing according to the present invention can be carried out in any container, including but not limited to, tanks. The container may be totally closed, or vented, or may be equipped for a continuous flow of the medium which is to contact the material into and out of the container. Two or more of these conditions may exist in the container at different times over the course of a measurement operation.

The relation between the concentration of noble gas which is measured and the corresponding material corrosion rate can be determined with the aid of suitable computer programming. Such programming could be developed on the basis of calibration measurements indicating the relationship in question and known programming techniques.

If the material whose corrosion is being tested is installed in, or forms the wall of, a tank filled with a liquid medium, the noble element gas liberated from the material as a result of corrosion will be measured when it enters into mixture in the gas provided at the headspace of the container. In this case, the measuring operation according to the invention will be improved by providing a system for recirculating gases from the headspace into the liquid medium in the tank. The purpose of this would be to promote a more complete transfer of the noble element gas from the liquid medium into the gaseous medium in the headspace. By way of example, use may be made of a known level measuring system which introduces gases below the surface of the liquid in a tank to, in effect, provide a continuous purge of dissolved gases within the tank.

In order to confirm the rate and uniformity of mixing of the noble element gas with other gases in a headspace, for a particular installation or tank, the concentration profile of a different gas may be examined according to techniques known in the art.

For various material compositions, implanting of noble element gas ions or atoms could cause damage to the crystalline structure of the material. In such cases, the surface into which the noble element gas has been implanted could be covered with one or more additional layers of the material to be tested. Corrosion will then be monitored by allowing the corroding medium to contact an exposed surface of the additional layer.

An embodiment of such a test structure, or sample, is shown in FIG. 2 where a layer 8 of the same material as body 2 is deposited on body 2 after a noble element gas has been implanted in region 4 of body 2, as shown in FIG. 1.

Layer 8 covers the top surface of body 2 into which a gas has previously been implanted and the thickness of layer 8 on that surface is accurately measured prior to testing.

In accordance with the invention, the test structure of FIG. 2 is arranged and/or fabricated to assure that corrosion will occur through layer 8 covering the surface of body 2 into which a gas has been implanted before the corroding medium can reach region 4 from the bottom or sides of body 2. For example, to prevent the corroding medium from prematurely reaching the sides of body 2, layer 8 extends along those sides and is made thicker along the sides than at the top of body 2. To prevent the corroding medium from prematurely reaching the region 4 via the bottom surface of body 2, either the bottom surface may be placed against a wall or other member to isolate the bottom surface from the corroding medium, or body 2 may be made sufficiently thick that the portion of body 2 between the bottom surface and level 6 is thicker than layer 8 at the top surface of body 2.

Another sample arrangement for use in the practice of the present invention is shown in FIG. 3. This sample is composed of a substrate 10 enclosed by a layer 12 of the material whose corrosion resistance is to be observed.

Substrate 10 can be of any material and is preferably a material having the following two characteristics: it provides a satisfactory matrix for receiving a noble element gas; and it is easily and rapidly corroded by the medium employed to determine the corrosion property of the material of layer 12.

The sample shown in FIG. 3 is prepared by embedding or implanting a selected noble element gas in substrate 10 and then enclosing substrate 10 in layer 12 of the material whose corrosion resistance is to be tested. The thickness of layer 12 is accurately determined prior to testing and the sample is then brought into contact with the selected corroding medium.

When layer 12 has been corroded down to substrate 10, the implanted noble element gas is released at a high rate, due to rapid corrosion or dissolution of substrate 10, resulting in an incremental increase in the concentration of noble element gas which is subsequently detected.

According to a further feature of the invention, a plurality of samples having the form shown in FIG. 2 or 3 may be prepared. In the case of the embodiment of FIG. 2, the thickness of layer 8 at the top surface of body 2 differs from one sample to another, this thickness of each layer being accurately measured prior to testing. In the case of the embodiment of FIG. 3, all samples have an identical substrate 10, but the thickness of layer 12 differs from one sample to another. The layer 12 of all samples is made of the same material. Here again, the thickness of the layer of each sample is accurately measured prior to testing.

All samples are then brought into contact with the selected corroding medium and as the medium penetrates the layer 12 of each sample, starting from the sample with the thinnest layer, there occur successive incremental jumps in the rate of delivery of noble element gas to the measuring location. Thus, each jump in the measured noble element gas concentration is indicative that layer 12 of the sample having the next succeeding layer thickness has been corroded down to its associated substrate 10.

Use of the sample embodiments shown in FIGS. 2 and 3, and particularly FIG. 3, offers a number of advantages. For example, it allows appropriate testing of sample materials which may be damaged by implantation of a noble element gas, in which case the corrosion properties of the material would be altered. In addition, it allows detection of corrosion depths greater than the depth to which detectable quantities of a noble element gas can be implanted.

Specialized samples according to the invention can further be produced by implanting, with an isotope separator, a noble element gas in a specific phase, surface or crystal phase of a sample material so that corrosion in that specific phase, surface, or crystal phase can be examined.

Since $^{85}$kr has a half life of longer than 10 years and undergoes primarily $\beta^-$ decay, it is particularly suitable for long term studies. Other radioisotopes may be selected which have shorter half-lives or which emit even less $\gamma$ radiation, so that after a reasonably short time, very little of the radioisotope remains and it therefore does not present a radiation hazard.

If, after a period of time, no corrosion is detected, operation of the measuring equipment can be tested by placing the sample or samples in contact with a medium known to be corrosive with respect to the sample material and effecting detection of liberated gas.

A measurement performed according to the invention involves adding to a measuring region a detectable substance that was not previously present. Under these circumstances, very small concentrations of the substance can be measured.

The noble gas employed in the practice of the invention may be radioactive or nonradioactive. In the case of a radioactive gas, such as $^{85}$Kr, the gas may be present in a sealed enclosure which is physically isolated from the detector, e.g. a scintillation counter. In the case of a nonradioactive gas, such as $^3$He or $^4$He, the gas will be permitted to flow to the measuring region of the detector, e.g. a mass spectrometer.

The invention can perform the desired test in a relatively small container since useful results can be achieved with a small sample and a small quantity of corroding medium.

The invention can be employed either to measure the corrosion rate of a sample exposed to a corroding medium having known corrosive characteristics, or to measure the corrosion rate of a sample having a known corrosion rate by a medium whose corrosivity is to be determined.

According to an exemplary embodiment, the corrosivity of a medium is measured in a small container by placing a foil of a standard test sample material, such as SAE 1020 steel, and a suitable quantity of the medium in the container. The sample may have the form shown in FIG. 1 and prior to introduction of the sample into the container, a noble gas is implanted into the sample down to a depth of a few angstroms. After introduction of the sample and medium into the container, the container is placed in a suitable test enclosure which is provided with a detector, such as one of the detectors referred to earlier herein, and liberation of the implanted noble gas from the sample is monitored.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for determining the corrosion behavior of a material with respect to a medium in contact with the material, comprising:

implanting a substantially chemically inert gas in a matrix so that corrosion experienced by the material causes the inert gas to enter the medium;

placing the medium in contact with the material; and measuring the amount of inert gas which enters the medium.

2. A method as defined in claim 1 wherein the material has a surface with which the medium is placed in contact, and the matrix is formed by a region of the material which extends from the surface.

3. A method as defined in claim 2 wherein the inert gas is a radioactive noble element gas.

4. A method as defined in claim 3 wherein the noble element gas is $^{85}$Kr.

5. A method as defined in claim 1 wherein the material has the form of a sheet disposed against a surface of a substrate, the matrix is formed by the substrate, and the sheet of material is interposed between the surface of the substrate and the medium.

6. A method as defined in claim 5 wherein the inert gas is a radioactive noble element gas.

7. A method as defined in claim 6 wherein the noble element gas is $^{85}$Kr.

8. A method as defined in claim 5 wherein the material has the form of a plurality of sheets having respectively different thicknesses, each sheet being disposed against a respective surface of a substrate, the matrix is formed by each substrate, and each sheet of material is interposed between the surface of a substrate and the medium.

9. A test sample of a material whose corrosion rate by a medium is to be measured, comprising:

a body of the material, which body has a surface to be contacted by the medium; and a substantially chemically inert gas implanted into the body to a depth below the surface.

10. A test sample as defined in claim 9 wherein the inert gas is a radioactive noble element gas.

11. A test sample as defined in claim 10 wherein the noble element gas is $^{85}$Kr.

12. A test sample as defined in claim 9, wherein the material of the body is SAE 1020 steel.

13. A test sample as defined in claim 9 further comprising a layer of the material disposed on said surface of said body.

14. A test sample of a material whose corrosion rate by a medium is to be measured, comprising:

a substrate of material which is easily corroded by the medium, the substrate having a surface;

a substantially chemically inert gas implanted into said substrate; and a layer of the material whose corrosion rate is to be measured, said layer being disposed against said surface of said substrate and having a defined thickness.

15. A test sample as defined in claim 14 wherein the inert gas is a radioactive noble element gas.

16. A test sample as defined in claim 15 wherein the noble element gas is $^{85}$Kr.

17. A test sample as defined in claim 14 wherein the material of said layer is SAE 1020 steel.

* * * * *